United States Patent
Kwon et al.

[11] Patent Number: 5,627,282
[45] Date of Patent: May 6, 1997

[54] PROCESS FOR THE PREPARATION OF OPTICALLY PURE 1,2,3,4-TETRAHYDRO-3-ISOQUINOLINECARBOXYLIC ACID AND ITS DERIVATIVES

[75] Inventors: Taesoo Kwon, Flanders; Francis J. Taplin, Caldwell, both of N.J.

[73] Assignee: Yukong Limited, Seoul, Rep. of Korea

[21] Appl. No.: 582,497

[22] Filed: Jan. 3, 1996

[51] Int. Cl.⁶ .................................................. C07D 217/26
[52] U.S. Cl. ............................................................ 546/147
[58] Field of Search .............................................. 546/147

[56] References Cited

U.S. PATENT DOCUMENTS 4,912,221  3/1990  O'Reilly et al. .................... 546/147

FOREIGN PATENT DOCUMENTS

| 0093804 | 4/1981 | European Pat. Off. . |
| 0260118 | 9/1987 | European Pat. Off. . |
| 2193969 | 7/1990 | Japan . |
| 9405640 | 3/1994 | WIPO . |

OTHER PUBLICATIONS

Miyake et al. "Takeda Research Laboratory", 43 (314), 53–76 (1984).
Kammermeier et al. "Synthesis", Nov., 1992 1157–1160.

*Primary Examiner*—Zinna Northington Davis
*Attorney, Agent, or Firm*—Abelman, Frayne & Schwab

[57] ABSTRACT

This invention relates to the preparation of optically pure tetrahydro-3-isoquinolinecarboxylic acid derivative of formula (III) which comprises the reaction of optically pure phenylalanine derivative of formula (I) with a formaldehyde precursor, such as formaline, trioxane, dialkoxymethane, or paraformaldehyde, for about 10 hours to 60 hours at about 40 ° C. to about 60 ° C. in concentrated hydrochloric acid to give the compound of formula (II), followed by neutralization in hot water at about 70 ° C. to about 100 ° C. with a base, such as ammonium hydroxide, potassium carbonate, sodium carbonate, sodium hydroxide or potassium hydroxide, according to the following reaction scheme.

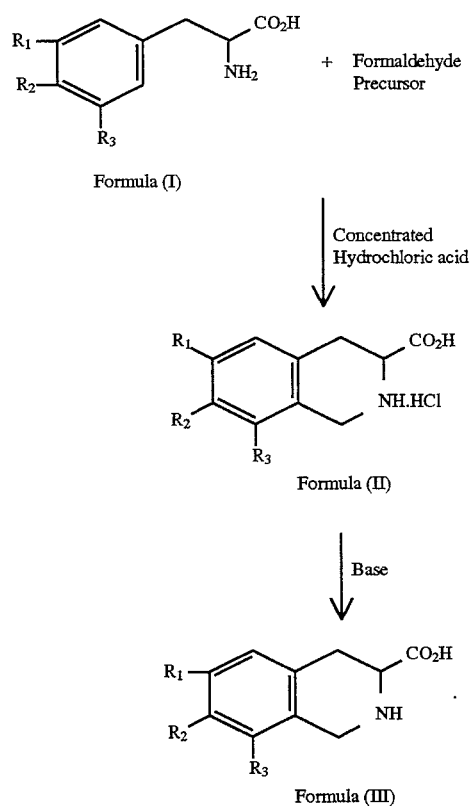

4 Claims, No Drawings

PROCESS FOR THE PREPARATION OF OPTICALLY PURE 1,2,3,4-TETRAHYDRO-3-ISOQUINOLINECARBOXYLIC ACID AND ITS DERIVATIVES

BACKGROUND OF THE INVENTION

The present invention relates to a convenient process for the preparation of optically pure 1,2,3,4-tetrahydro-3-isoquinolinecarboxylic acid and its derivatives. More specifically, the invention pertains to a method for producing optically pure 1,2,3,4-tetrahydro-3-isoquinolinecarboxylic acid and its derivatives through the reaction of optically pure phenylalanine and its derivatives with a formaldehyde precursor, such as, for example formaline, trioxane, dialkoxymethane or paraformaldehyde in 37% concentrated hydrochloric acid followed by neutralization.

(L)-1,2,3,4-tetrahydro-3-isoquinolinecarboxylic acid is a non-natural amino acid useful for the synthesis of ACE inhibitor (Miyake et al. J. Takeda Res. Lab. 1984, 43, 53; Suj et al. Eur. Patent-A 39804; Arzeno et al. Eur. Patent-A 260118) and bradykinin antagonists (Henke et al. Eur. Patent-A 0370453; Hook et al. J. Pharmacol. 1991, 102, 769; J. Pharmacol. 1991, 114, 297).

In general, racemization and low yields are known to be the major drawbacks of Pictet-Spengler cyclization for the synthesis of optically pure 1,2,3,4-tetrahydro-3isoquinolinecarboxylic acid from optically pure phenylalanine (Julian et al. J. Am. Chem. Soc. 1948, 70, 182; Archer J. Org. Chem 1961, 16, 430; Hein et al. J. Am. Chem Soc. 1962, 84, 4487; Shinkai et al. J. Med. Chem. 1988, 31, 2092).

Recently, Soeda et al. (JP 02193969) reported that (L)-1,2,3,4-tetrahydro-3isoquinolinecarboxylic acid hydrochloric acid salt of optical purity 59.7–85.4% e.e. was obtained in 45.6–85.4% yields from the reaction of optically pure (L)-phenylalanine with paraformaldehyde in concentrated hydrochloric acid. However, this process is inefficient in the view of the low yields and the low optical purities of the product.

Kuge et al. reported that (L)-1,2,3,4-tetrahydro-3-isoquinolinecarboxylic acid hydrobromic acid salt of optical purity 97% e.e. was obtained in 87.4% yield from the reaction of (L)-phenylalanine with formaldehyde or paraformaldehyde in 37% concentrated hydrobromic acid. However, this process has the disadvantages in the cost and the waste treatment of hydrobromic acid. Moreover, the effect of the repetitive use of hydrochloric acid, hydrobromic acid and other inorganic acids or organic acids have not as yet been reported.

In order to overcome these disadvantages, it would be desirable to provide an efficient process for the preparation of 1,2,3,4-tetrahydro-3-isoquinolinecarboxylic acid of high optical purity using hydrochloric acid which is economical to use and provides for ease of waste treatment.

SUMMARY OF THE INVENTION

The present invention is directed to (i) the development of an efficient process to provide 1,2,3,4-tetrahydro-3-isoquinolinecarboxylic acid hydrochloric acid salt or its derivatives of high optical purity and good yield which comprises the reaction of optically pure phenylalanine or its derivatives with a formaldehyde precursor, such as formaline, trioxane, dialkoxymethane or paraformaldehyde, at low temperature in concentrated hydrochloric acid; (ii) the minimization of waste generation, and (iii) the development of an efficient neutralization method to provide optically pure 1,2,3,4-tetrahydro-3-isoquinolinecarboxylic acid and its derivatives which can be used as an important pharmaceutical intermediate in the synthesis of acetylcholin esterase (ACE) inhibitor and bradykinin antagonist.

DETAILED DESCRIPTION OF THE INVENTION

The present invention is described in the following reaction scheme:

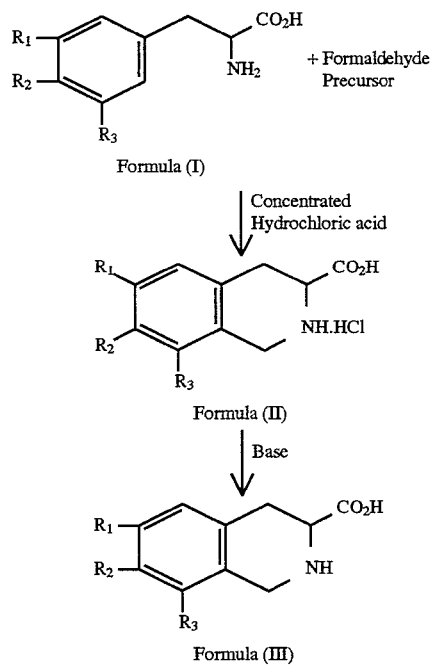

(L)-Phenylalanine, 1,2,3,4-tetrahydro-3-isoquinolinecarboxylic acid hydrochloric acid salt, and 1,2,3,4-tetrahydro-3-isoquinolinecarboxylic acid or their derivatives have the formulas (I), (II), and (III), respectively: wherein $R_1$ and $P_2$ are H, alkyl of $C_1$ to $C_7$, alkoxy of $C_1$ to $C_7$, —$OCH_2O$—, or halogen, suitably fluorine, chlorine, bromine, and iodine; $R_3$ is H or alkoxy of $C_1$ to $C_6$.

The suspension of an optically pure compound of formula (I) and a formaldehyde precursor, such as formaline, trioxane, dialkoxymethane or paraformaldehyde (4 to 20 equivalents), in 37% hydrochloric acid is heated at a certain temperature, suitably between about 40° C. to about 60° C. After a certain period of time, suitably between about 10 hours to about 60 hours, the conversion is determined by High Pressure Liquid Chromatography (HPLC). Then, the reaction mixture was cooled to about 0° C. The precipitate is filtered out, washed with cold water, a $C_1$ to $C_3$ alkyl alcohol, or acetone, and dried under vacuum.

The obtained yield for the compound of formula (II) is between about 75% to about 86% and the optical purity for the compound of formula (II) is between about 90% to about 97% enantiomeric excess (e.e). Moreover, the concentrated hydrochloric acid filtrate is used repetitively, i.e., recycled, because it contains products and starting materials. The yield of the product of formula (II) is increased from about 91% to about 97%.

The compound of formula (III) is obtained by neutralization of the compound of formula (II) to a pH between about 6 to about 7 with a base in hot water at a temperature of about 70° C. to about 100° C. The obtained yield of the compound of formula (III) is between about 94% to about 96% and its optical purity is greater than 99% e.e. The bases used above are, for example, sodium hydroxide, ammonium hydroxide, potassium carbonate, or potassium hydroxide. Naturally, the forgoing bases are only exemplary of the bases that can be employed.

The present invention has the following advantages over the prior art Soeda et al. JP 02193969 reference. First, the reaction is carried out at lower temperature so as to minimize racemization. As a result, the compound of formula (II) is obtained in high optical purity between about 90% to about 97%. Second, the compound of formula (III) with an optical purity greater than 99% e.e. is easily obtained in about 94% to about 96% yield, without purification, merely by neutralization in hot water. Third, the repetitive use of concentrated hydrochloric acid filtrate not only increases the yield of the compound of formula (II), it also minimizes the generation of hazardous waste.

The following examples are illustrative embodiments of this invention. However, these examples are for illustrative purposes only and should not be construed as limitations upon the invention.

The progress of the reaction was monitored by HPLC with Lichrospher 100 RP-18 column (Hewlett-Packard). Optical purity was measured by HPLC with Chiralpak WH column (Chiral Technologies Inc.).

EXAMPLE 1.

(L)-phenylalanine (1 equivalent) and paraformaldehyde (4 equivalent), as described in experiment 1 of Table 1 below, was added to 20 mL of 37% concentrated hydrchloric acid and heated at 50° C. for 50 hours. The reaction mixture was cooled to 0° C. and white crystalline solid was filtered out. After washing with cold water and acetone, and drying, 2.20 g (86% yield) of white crystalline (L)-tetrahydro-3-isoquinolinecarboxylic acid hydrochloric acid salt was obtained ($R_1, R_2, R_3$ =H, 96% e.e.).

EXAMPLES 2–5.

Instead of fresh 37% concentrated hydrochloric acid, the filtrate generated in the previous experiment was used after resaturation with gaseous hydrogen chloride. (L)-Phenylalanine and paraformaldehyde were added to the above filtrate in the ratio of 1:1. Besides these changes, (L)-tetrahydro-3-isoquinolinecarboxylic acid hydrochloric acid was prepared as described in the Example 1. The results are described in Table 1.

TABLE 1

Yield improvement of (L)-tetrahydro-3-isoquinolinecarboxylic acid preparation by the repetitive use of concentrated hydrochloric acid filtrate

| Example | (L)-Phenyl-alanine | Paraformal-dehyde | Yield (%) | Optical purity (% e.e.) |
| --- | --- | --- | --- | --- |
| 1 | 2.0 g | 1.45 g | 85 | 96 |
| 2 | 2.0 g | 0.36 g | 91 | 97 |
| 3 | 2.0 g | 0.36 g | 95 | 94 |
| 4 | 2.0 g | 0.36 g | 97 | 95 |
| 5 | 2.0 g | 0.36 g | 93 | 96 |

As can be seen in Table 1, the repetitive use of concentrated hydrochloric acid does not affect the optical purity of the product and improves the yield to the extent of about 6% to about 12%.

EXAMPLE 6.

The product of Example 1 was dissolved in 20 mL of boiling water, and neutralized to a pH between about 6 to 7 with 30% aqueous ammonium hydroxide. After the reaction mixture was cooled to 0° C., the white crystalline product was filtered, washed with cold water, ethanol and acetone. After drying in a vacuum oven, 1.75 g (96%) of (L)-tetrahydro-3-isoquinolinecarboxylic acid with an optical purity greater than 99% e.e. was obtained.

EXAMPLE 7.

(L)-phenylalanine (2.01 g, 12.20 mmol) and formaline (3.96 g, 48.8 mmol) was added to 20 mL of 37% concentrated hydrochloric acid and heated at 60° C. for 24 hours. The reaction mixture was cooled to 0° C. and white crystalline solid was filtered out. After washing with cold water and acetone, and drying, 2.04 g (78% yield) of white crystalline (L)-tetrahydro-3-isoquinolinecarboxylic acid hydrochloric acid salt was obtained ($R_1, R_2, R_3$=H, 95% e.e.). This product was dissolved in 20 mL of boiling water, and neutralized to a pH between about 6 to about 7 with 30% aqueous ammonium hydroxide. After the reaction mixture was cooled to 0° C., the white crystalline product was filtered, washed with cold water, ethanol and acetone. After drying in a vacuum oven, 1.61 g (95%) of (L)-tetrahydro-3-isoquinolinecarboxylic acid with an optical purity greater than 99% e.e. was obtained.

EXAMPLE 8.

(L)-phenylalanine (10.00 g, 61.00 mmol) and trioxane (10.90 g, 122.0 mmol) were added to 90 mL of 37% concentrated hydrochloric acid and heated at 50° C. for 40 hours. The reaction mixture was cooled to 0° C. and white crystalline solid was filtered out. After washing with cold water and acetone, and drying, 10.40 g (80% yield) of white crystalline (L)-tetrahydro-3-isoquinolinecarboxylic acid hydrochloric acid salt was obtained ($R_1, R_2, R_3$ =H, 96% e.e.). This product was dissolved in 90 g of boiling water, and neutralized to pH between about 6 to about 7 with 30% aqueous ammonium hydroxide. After the reaction mixture was cooled to 0° C., the white crystalline product was filtered, washed with cold water, ethanol and acetone. After drying in a vacuum oven, 8.20 g (95%) of (L)-tetrahydro-3-isoquinolinecarboxylic acid with an optical purity greater than 99% e.e. was obtained.

EXAMPLE 9.

(L)-phenylalanine (2.01 g, 12.20 mmol) and dimethoxymethane (27.60 g, 122.0 mmol) were added to 90 mL of 37% concentrated hydrchloric acid and heated at 50° C. for 24 hours. The reaction mixture was cooled to 0° C. and white crystalline solid was filtered out. After washing with cold water and acetone, and drying, 9.70 g (75% yield) of white crystalline (L)-tetrahydro-3-isoquinolinecarboxylic acid hydrochloric acid salt was obtained ($R_1, R_2, R_3$ =H, 96% e.e.). This product was dissolved in 90 mL of boiling water, and neutralized to a pH between about 6 to about 7 with 30% aqueous ammonium hydroxide. After the reaction mixture was cooled to 0° C., the white crystalline product was filtered, washed with cold water, ethanol and acetone. After drying in a vacuum oven, 7.72 g (95%) of (L)-tetrahydro-3-isoquinolinecarboxylic acid with an optical purity greater than 99% e.e. was obtained.

EXAMPLE 10.

(L)-phenylalanine (2.01 g, 12.20 mmol) and formaline (3.96 g, 48.8 mmol) were added to 20 mL of 37% concentrated hydrchloric acid and heated at 60° C. for 24 hours. The reaction mixture was cooled to 0° C. and white crystalline solid was filtered out. After washing with cold water and acetone, and drying, 2.04 g (78% yield) of white crystalline (L)-tetrahydro-3-isoquinolinecarboxylic acid hydrochloric acid salt was obtained ($R_1, R_2, R_3$ =H, 91% e.e.). This product was dissolved in 20 mL of boiling water, and neutralized to a pH between about 6 to about 7 with 30% aqueous ammonium hydroxide. After the reaction mixture was cooled to 0° C., the white crystalline product was filtered, washed with cold water, ethanol and acetone. After drying in a vacuum oven, 1.61 g (95%) of (L)-tetrahydro-3-isoquinolinecarboxylic acid with an optical purity greater than 99% e.e. was obtained.

EXAMPLE 11.

(L)-4-Methoxy-phenylalanine (2.38 g, 12.20 mmol) and formaline (3.96 g, 48.8 mmol) were added to 20 mL of 37% concentrated hydrchloric acid and heated at 60° C. for 24 hours. The reaction mixture was cooled to 0° C. and the white crystalline solid was filtered out. After washing with cold water and acetone, and drying, 2.38 g (80% yield) of white crystalline (L)-7-methoxy-tetrahydro-3-isoquinolinecarboxylic acid hydrochloric acid salt was obtained ($R_1, R_2, R_3$ =H, 91% e.e.). This product was dissolved in 20 mL of boiling water, and neutralized to a pH between about 6 to about 7 with 30% aqueous ammonium hydroxide. After the reaction mixture was cooled to 0 ° C., the white crystalline product was filtered, washed with cold water, ethanol and acetone. After drying in a vacuum oven, 1.92 g (95%) of (L)-tetrahydro-3-isoquinolinecarboxylic acid with an optical purity greater than 99% e.e. was obtained.

What is claimed is:

1. A process for the preparation of an optically pure tetrahydro-3-isoquinolinecarboxylic acid derivative of formula (III) which comprises the reaction of an optically pure phenylalanine derivative of formula (I) with a formaldehyde precursor for about 10 hours to 60 hours at about 40° C. to about 60° C. in concentrated hydrochloric acid to give the compound of formula (II), followed by neutralization in hot water at about 70° C. to 100° C. with a base in accordance with the following reaction scheme:

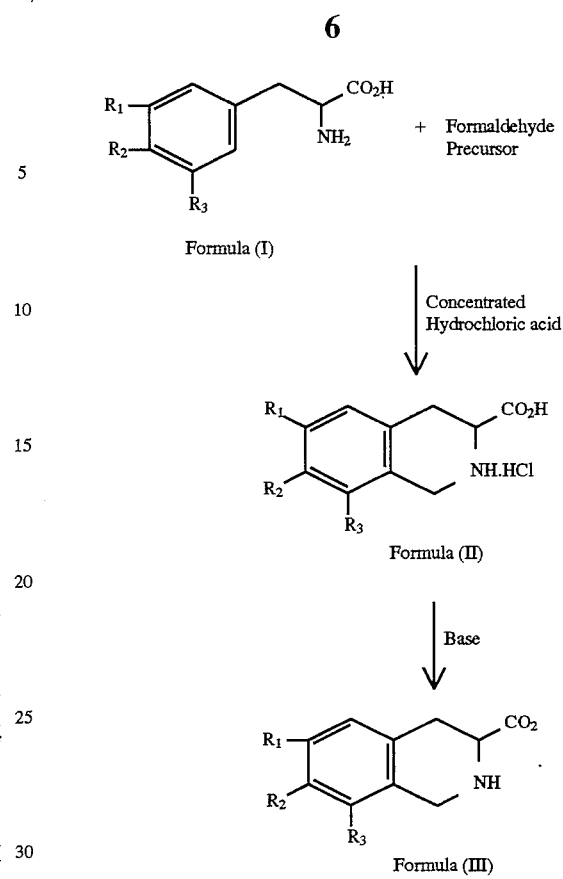

wherein in formula (I), (II), and (III): $R_1$ and $R_2$ are H, alkyl of $C_1$ to $C_7$, alkoxy of $C_1$ to $C_7$ —$OCH_2O$—, or halogen, which is selected from fluorine, chlorine, bromine, and iodine; $R_3$ is H or alkoxy of $C_1$–$C_6$.

2. The process of claim 1 wherein the concentrated hydrochloric acid filtrate is recycled for reuse.

3. The process of claim 1 wherein the base is selected from the group consisting of ammonium hydroxide, potassium carbonate, sodium carbonate, sodium hydroxide or potassium hydroxide.

4. The process of claim 1 wherein the formaldehyde precursor is selected from the group consisting of formaline, trioxane, dialkoxymethane or paraformaldehyde.

* * * * *